United States Patent [19]

Yoshizumi et al.

[11] Patent Number: 4,497,799
[45] Date of Patent: Feb. 5, 1985

[54] POLYPEPTIDE CARCINOSTATIC AGENT

[75] Inventors: Hajime Yoshizumi; Kumao Toyoshima; Akira Hakura; Toshihiro Nakanishi, all of Osaka, Japan

[73] Assignee: Suntory Ltd., Osaka, Japan

[21] Appl. No.: 319,755

[22] Filed: Nov. 9, 1981

[51] Int. Cl.³ .................... A61K 37/00; C07C 103/52
[52] U.S. Cl. ................................. 514/9; 260/112.5 R
[58] Field of Search .................. 260/112.5 R; 424/177

[56] References Cited

U.S. PATENT DOCUMENTS 4,287,185 9/1981 Toyoshima et al. ......... 260/112.5 R

FOREIGN PATENT DOCUMENTS 55-50897 4/1980 Japan ........................... 260/112.5 R

OTHER PUBLICATIONS

Computer Printout.
Cereal Chemistry (1977), vol. 54, No. 3, 511–523.
Journal Canadien de Biochimie, vol. 54, No. 10 (1976) 835–842.

Primary Examiner—Delbert R. Phillips
Attorney, Agent, or Firm—Sughrue, Mion, Zinn, Macpeak, and Seas

[57] ABSTRACT

A carcinostatic agent containing a polypeptide of the formula

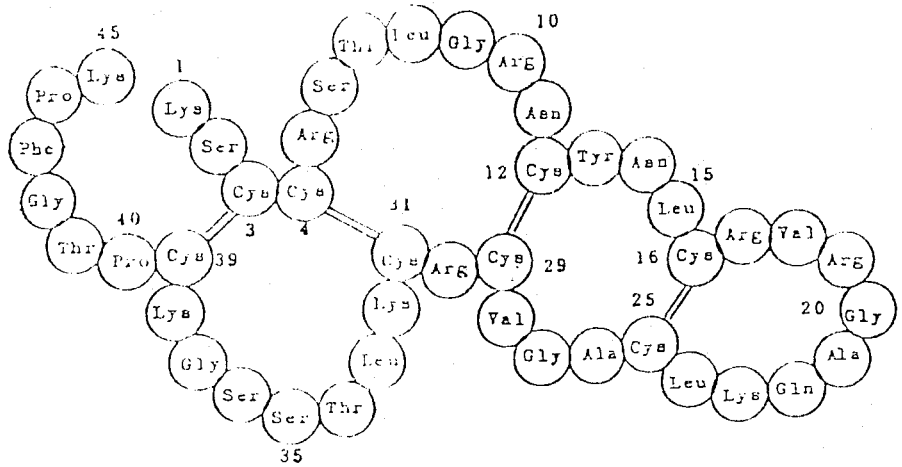

5 Claims, 3 Drawing Figures

POLYPEPTIDE CARCINOSTATIC AGENT

BACKGROUND OF THE INVENTION

The present invention relates to a particular polypeptide which can be extracted from various cereal grains and then used in extracted form, preferably after being purified, as a carcinostatic agent.

SUMMARY OF THE INVENTION

The invention relates to a polypeptide having the following primary formula

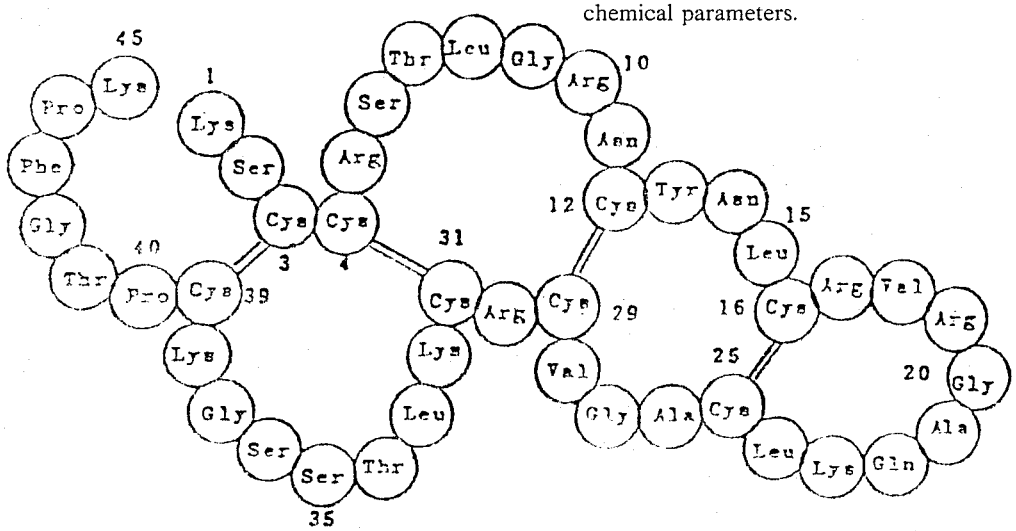

wherein Ala, Arg, Asn, Cys, Gln, Gly, Leu, Lys, Phe, Pro, Ser, Thr, Tyr and Val represent the amino acid residues of the L-forms of alanine, arginine, asparagine, ½ cystine, glutamine, glycine, leucine, lysine, phenylalanine, proline, serine, threonine, tyrosine and valine, respectively; the designation "=" represents a —S—S— bond and the arabic numbers adjacent to the amino acid cords depict the amino acid sequential arrangement as enumerated from the N-terminal; and further relates to a carcinostatic agent including such polypeptide (hereafter referred to as "SPH") as the effective agent thereof.

In other embodiments of this invention, there are provided pharmaceutical preparations comprising a carcinostatic effective amount of SPH and a pharmaceutically acceptable carrier, and a method for inhibiting the growth of cancerous cells by administering an inhibitory amount of SPH. Accordingly, it is an object of this invention to provide a novel pharmaceutical carcinostatic agent comprising a defined polypeptide as the active ingredient thereof.

A further object of this invention is to provide a method to inhibit the growth of cancerous cells.

Another object of this invention is to provide a defined polypeptide found in certain cereal grains in extracted and/or substantially pure form.

DETAILED DESCRIPTION OF THE INVENTION

The polypeptide used in the present invention is composed of 45 amino acid units forming in part a peculiar configuration of four closed rings in which the polypeptide compound is bridged with four disulfide bonds between the 3rd and 39th, the 4th and 31st, the 12th and 29th, and the 16th and 25th cysteine pairs, thereby forming the four closed rings. SPH is unusual in view of its abnormal high content of cysteine, lysine and arginine and the lack of methionine, tryptophan and histidine. SPH has been characterized by the following physicochemical parameters.

PHYSICO-CHEMICAL PROPERTIES OF SPH

Appearance: colorless needles.
Isoelectric point: ca. 10
Molecular weight: can be calculated to be 4848 from the data of amino acid arrangement discussed hereinafter.
Number of constituent amino acids: 45
Amino acid arrangement

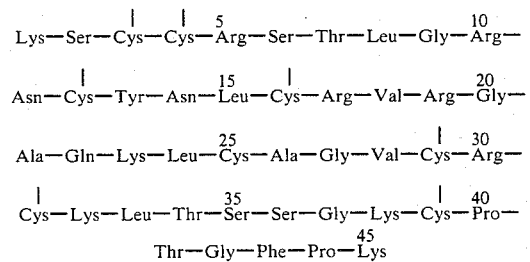

The significance of the respective amino acid cords is as described herein. The numbered sequence sets forth the order of amino acid arrangement.

Elemental analysis:

|  | C | H | N | S |
|---|---|---|---|---|
| Calculated: | 49.32 | 6.90 | 19.66 | 5.29 |
| Found: | 49.08 | 7.00 | 19.51 | 5.42 |

Figure 1:
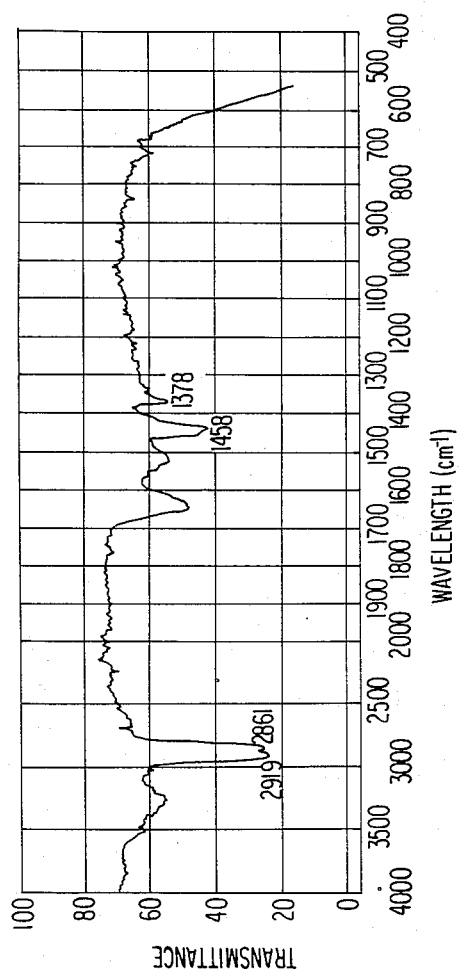
FIG. 1 of the Drawings is an ultraviolet absorption spectrum of SPH.

Ultraviolet spectrum: a specific absorbance at ca. 278 nm due to the peptide linkage. (See FIG. 1 of the Drawings.) (The sample was measured using a HITACHI Double Beam Spectrophotometer-356.)

Figure 2:
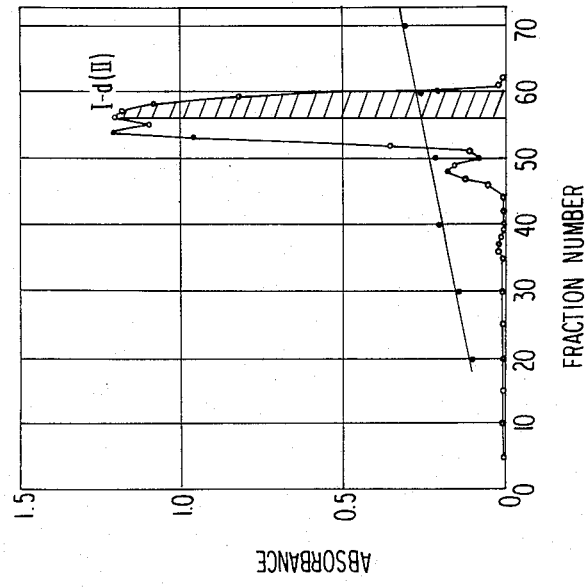
FIG. 2 of the Drawings is an infrared absorption spectrum of SPH.

Infra-red spectrum: a specific absorbance at ca. 1650 cm$^{-1}$ due to the peptide structure. (See FIG. 2 of the Drawings.) (Measured using a HITACHI Grating Type Infra-red spectrophotometer.)

Amino acid constitution: (see Table 1, below)

TABLE 1

| Amino Acid | μmol (Calculated)* | Number of Residues Presumed |
| --- | --- | --- |
| AsX (Asp + Asn) | 1.97 | 2 |
| Thr | 3.11 | 3 |
| Ser | 4.02 | 4 |
| GlX (Glu + Gln) | 1.04 | 1 |
| Pro | 2.01 | 2 |
| Gly | 4.79 | 5 |
| Ala | 2.07 | 2 |
| ½ Cys | 7.34 | 8** |
| Val | 1.98 | 2 |
| Met | — | 0 |
| Ile | — | 0 |
| Leu | 3.97 | 4 |
| Tyr | 0.82 | 1** |
| Phe | 0.99 | 1 |
| Lys | 5.17 | 5 |
| His | — | 0 |
| Arg | 5.24 | 5 |
| Trp*** | — | 0 |

*Samples were hydrolyzed with 6N HCl at 110° C. in a sealed tube and then measured using an Amino acid Analyzer, available from NIPPON DENSHI, Type JLC 5.
**This data was obtained from analysis of amino acid arrangement.
***Measured by spectrophotometry.

Gel-Electrophoresis: Polyacrylamide gel-disc-electrophoresis only developed one band. (Method: The sample was electrophoretically migrated on 75% polyacrylamide gel (pH 9.4 and 4.0) at 25 mA/cm$^2$ for 50 minutes and then stained with 0.02% Coomasie brilliant blue R followed by washing with 10% trichloroacetic acid.)

EXISTENCE, EXTRACTION AND PURIFICATION OF SPH

SPH and analogs thereof are distributed widely in barley, wheat and rye. In wheat, SPH is most abundant in common wheat (*Triticum monococcum*) and in barley it is more abundant in *Hordeum agriocrithon* than in *H. spontaneum*. A method for obtaining SPH is illustrated by the following example.

EXAMPLE

4 Kg of powdered barley (*H. agriocrithon*) was suspended in 20 liters of 0.05N sulfuric acid and maintained at 30° C. for 3 hours. Then the mixture was centrifuged (at 3000 rpm, 10 minutes) at room temperature. The supernatant was collected, neutralized with 10N sodium hydroxide, allowed to stand for 12 hours at 5° C. and then centrifuged to remove formed insolubles. This second supernatant was collected and then loaded into a carboxymethylcellulose column (2.5×80 cm) equilibrated with 0.05M phosphate buffer solution of pH 7.2. Thereafter, the column was eluted with the above buffer solution in which the concentration of sodium chloride was linearly increased from 0.1M to 0.8M (flow rate was 55 ml/minute). The eluate was fractionated with a fraction collector according to a predetermined collected volume of 5 ml for each fraction. Optical density of each fraction was measured at once and fractions having maximum absorption at about 280 nm were combined and re-chromatographed through a second column of 1.5×75 cm and, if desired, finally freeze-dried. The yield was 343 mg.

Figure 3:
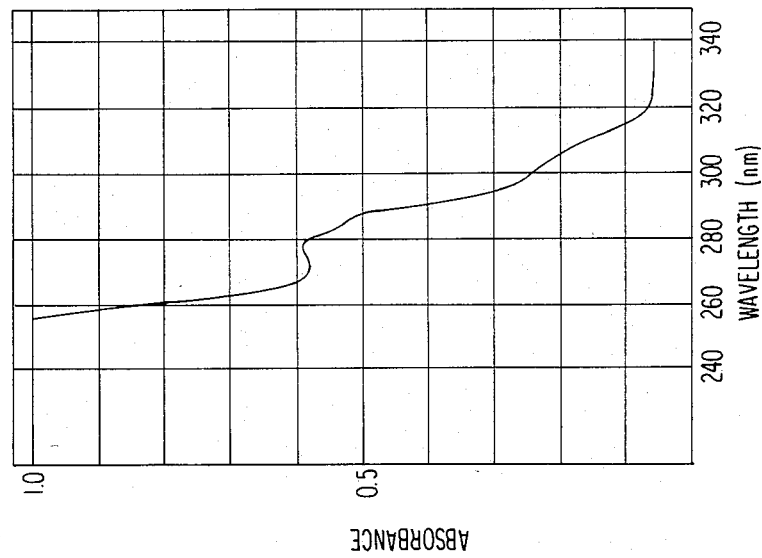
FIG. 3 of the Drawings is an elution curve of SPH.

The above dry sample (343 mg) was then loaded into another carboxymethylcellulose column (3.1×3.3 cm) buffered with 0.2M ammonium bicarbonate and then eluted with ammonium bicarbonate solution (pH 8.0) whose concentration was being changed from 0.2 to 0.8M under a flow rate of 66 ml/hr. The eluate was fractioned into 8 ml fractions and measurement of the absorption at 280 nm carried out on each fraction. In this particular example, fractions No. 56–60 were collected and then re-chromatographed as above, followed by freeze-drying. Yield 198 mg. (FIG. 3 of the Drawings is the elution curve of this particular example.)

CONFIRMATION OF CHEMICAL STRUCTURE

The chemical structure of SPH has been confirmed according to the following summary. The sample was preliminarily treated with performic acid so as to cut its disulfide linkages and then the Edman degradation procedure was carried out on this sample through 35 steps by a sequence analyzer by which the kind and binding order of amino acids from the lysine at the N-terminal through to the serine at position 35 in the sequence were confirmed. Then, the sample was hydrolyzed with trypsin, and the hydrolysate was fractioned into 15 fractions by chromatography and electrophoresis and each fraction was degraded using the Edman process so as to determine the amino acid arrangement of each fraction (peptide).

Another sample of SPH was alkylated, citraconylated, and then hydrolyzed with trypsin. This hydrolysate (alkylated and citraconylated peptides) was fractioned as above so as to determine the structure of each peptide fraction using the Edman process. The result was compared with the result of performulated peptide analysis above, and confirmed the establishment of the total amino acid arrangement from the N-terminal (No. 1, lysine) to the C-terminal (No. 45, lysine).

Next, in order to determine the positions of the disulfide linkages, an intact SPH sample was hydrolyzed with trypsin and thermolysin, and the hydrolysate thus obtained was fractionated to select fractions having —S—S— linkage by chromatography. These fractions were analyzed for amino acid content by Edman degradation after performylation.

PHARMACOLOGICAL ACTION OF SPH

SPH exhibits a marked growth inhibition effect against transformed cells (the cells which have been released from contact inhibition) in tissue culture tests. Namely, the growth of normal mouse cells (A$_{31}$ strain, control) were not effected in the presence of 2 ppm of SPH. To the contrary, the growth of tested transformed mouse cells (PV4) was markedly decreased, for example, to below 60% at 2 ppm, below 40% at 4 ppm and below 3.5% at 6 ppm of SPH.

As is well known, there are a few DNA type viruses which are suspected as being tumor causative agents at some point, such as Polioma virus SV 40 and Adeno virus. Moreover, it has been confirmed through animal experiments that when these viruses infect normal cells, the cells are transformed and can grow without limit. The strong inhibitory action of SPH to the growth of transformed cells may be because it inhibits self-DNA synthesis at the S-phase (which is the syntheses phase of DNA in the cell cycle) and therefore, the cell growth will be controlled in abnormal cells no longer having contact inhibition.

As described above, SPH has a specific action on the transformed cell. Therefore, it provides a hopeful expectation of use as a new carcinostatic agent because of this characteristic. The effect of SPH has been tested on EAC (Ehrlich ascites carcinoma), Sarcoma 180 A and Lymphocytic leukemia L 1210. It was found that SPH had a carcinostatic activity, for example, of marked inhibition against growth of EAC and Sarcoma 180 A cancerous cells in the abdominal fluid at a dose of 0.1–1.5 mg/Kg and increased the survival of the test animals against Lymphocytic leukemia. The experiments from which the above findings were derived and acute toxicity of SPH will be described in detail below.

(1) CARCINOSTATIC ACTION IN EXPERIMENTAL ANIMALS (1-a) (Materials)
 Animal: mouse (ICR)
 Cells: EAC and Sarcoma 180 A
(1-b) (Method)

Female mice (ICR, average body weight 25 g, age 5–6 weeks) were divided into 6 groups each consisting of 6 mice. Abdominal fluid of the mouse was inoculated with EAC or Sarcoma 180 A. Eight days after the inoculation, the inoculated fluid was diluted with physiological saline solution so as to contain $10^8$ cancerous cells per ml of the diluted cancerous cell solution. 0.1 ml of this solution was intraperitoneally injected into each mouse. One day later there was intraperitoneally administered 0.2 ml (corresponding to 0.1, 0.3, 0.5, 1.0 or 1.5 mg per Kg of the body weight) each of SPH for 5 days daily. Eight days after inoculation of the cancerous cells into the mice, the abdominal fluid was collected and the cell ratio (T/C%) calculated.

(1-c) (Results)
The results of the experiment are shown in Table 2, below.

TABLE 2

| Mouse Group | Inoculum | Dose of SPH | No. of Cells | T/C % | Decision |
|---|---|---|---|---|---|
| 1 | EAC | 0 (Control) | $5.18 \times 10^8$ | 100.0 | |
| 2 | EAC | 0.1 mg/Kg | $3.05 \times 10^8$ | 58.9 | + |
| 3 | EAC | 0.3 | $2.12 \times 10^8$ | 40.9 | +~++ |
| 4 | EAC | 0.5 | $2.35 \times 10^7$ | 4.5 | +++ |
| 5 | EAC | 1.0 | $1.84 \times 10^7$ | 3.6 | +++ |
| 6 | EAC | 1.5 | $1.33 \times 10^7$ | 2.6 | +++ |
| 1 | Sarcoma 180 A | 0 (Control) | $7.15 \times 10^8$ | 100.0 | |
| 2 | Sarcoma 180 A | 0.1 mg/Kg | $4.70 \times 10^8$ | 65.8 | + |
| 3 | Sarcoma 180 A | 0.3 | $3.02 \times 10^8$ | 42.3 | + |
| 4 | Sarcoma 180 A | 0.5 | $1.54 \times 10^8$ | 21.3 | ++ |
| 5 | Sarcoma 180 A | 1.0 | $1.06 \times 10^8$ | 14.8 | ++ |
| 6 | Sarcoma 180 A | 1.5 | $6.36 \times 10^7$ | 8.9 | +++ |

Standard of Decision
T/C % 100–66: −
65–41: +
40–11: ++
10–0: +++

As described in the above Table 2, it is seen that SPH has a strong tumor inhibitory action against EAC and Sarcoma 180 A.

The above experimental results indicate expected activity in humans.

(2) Acute toxicity in the mouse (2-1) (Materials)
 Animal: mouse (ICR, Swiss Albino and $BDF_1$)
(2-2) (Method)
 ICR (female, average body weight 25.0 g, age 5–6 weeks), Swiss Albino (female, average body weight 22.3 g, 5–6 weeks) and $BDF_1$ (female, average body weight 21.5, 6 weeks) were divided into 6 groups consisting of 6 mice each, and predetermined amounts of SPH dissolved in 0.2 ml of physiological saline were administered intraperitoneally.

(2-3) (Results)
The results are shown in Table 3, below. From the table it can be seen that the $LD_{50}$ of SPH is about 1.5 mg/Kg. Because the long term toxicity of SPH is low, the condition of the survival mice after recovery is similar to that of the control. Besides, from these results, it seems that an adequate daily dose of SPH will be below 1.0 mg/Kg, preferably, ca. 0.3 mg/Kg, and this dose would be subdivided into a fraction thereof to be administered a few times a day.

TABLE 3

| Mouse | | | | | |
|---|---|---|---|---|---|
| ICR | | Swiss Albino | | $BDF_1$ | |
| Dose and Numbers of died | | | | | |
| Dose mg/Kg | No. died (numerator) | Dose mg/Kg | No. died (numerator) | Dose mg/Kg | No. died (numerator) |
| 0.68 | 0/6 | 0.50 | 0/6 | 1.00 | 0/6 |
| 1.36 | 1/6 | 1.00 | 1/6 | 1.50 | 2/6 |
| 2.04 | 4/6 | 1.50 | 4/6 | 2.00 | 6/6 |
| 2.72 | 6/6 | 2.00 | 6/6 | 3.00 | 6/6 |

$LD_{50}$ ICR: 1.81 mg/Kg
Swiss Albino: 1.33 mg/Kg
$BDF_1$: 1.58 mg/Kg

The present invention is based on the above findings, and this invention involves both the use of SPH itself and a carcinostatic agent containing SPH as an effective ingredient thereof.

SPH can be used in pure or crude form, that is following extraction with or without additional purification, in the form of intravenous, intramuscular or intrasubcutaneous injectables or in oral form such as in solutions, tablets, granules, powders, troches, buccals and so on or in the form of other preparations for contact with mucous membranes such as vaginal or rectal suppositories, ointments or creams. Of course, any SPH preparation for injection should, preferably, be refined as much as possible. To obtain these preparations, pharmacologically common diluents, carriers, excipients, binders, vehicles and so on are used. A nontoxic vehicle such as a liquid fat or oil is suitable for compounding SPH into suspensions for injection. If need be, SPH can be modified into an acid-addition salt with any physiologically acceptable salt. For this purpose, an acid such as hydrochloric acid, hydrobromic acid, sulfuric acid, maleic acid, fumaric acid, lactic acid, citronic acid, tartaric acid, succinic acid and the like can be mentioned as suitable examples. A suitable dose for SPH is about 0.3–1.0 mg/Kg per day, but the practical dose will, naturally, be changed due to methods and forms of the administration.

While the invention has been described in detail and with reference to specific embodiment thereof, it will be apparent to one skilled in the art that various changes and modifications can be made therein without departing from the spirit and scope thereof.

We claim:
1. A method for inhibiting growth of transplanted tumors in mice comprising:
administering to said mice an antitumor effective amount of a composition comprising: (a) a polypeptide having the formula:

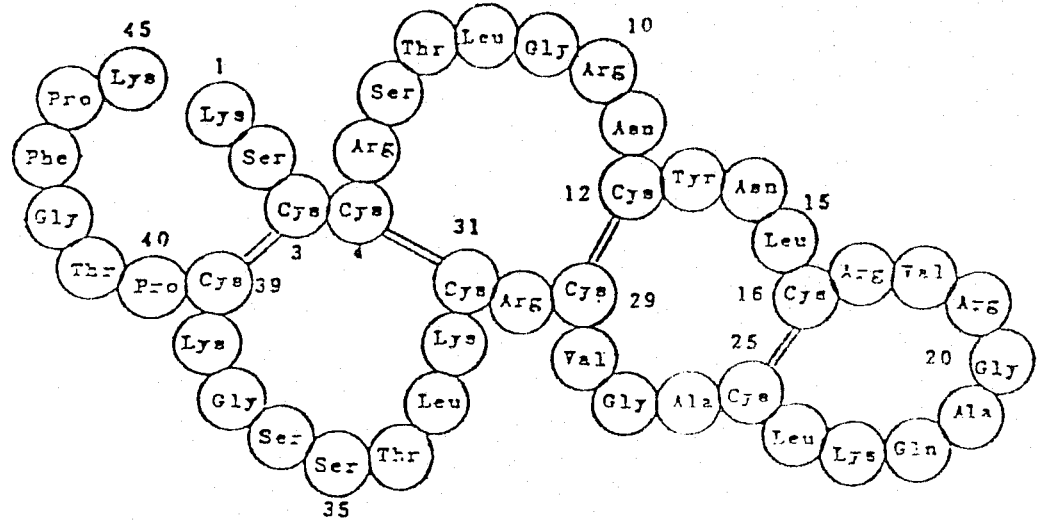

wherein the abbreviations, Ala, Arg, Asn, Cys, Gln, Gly, Leu, Lys, Phe, Pro, Ser, Thr, Tyr and Val represent the L-form residues of alanine, arginine, asparagine, ½ cysteine, glutamine, glysine, leucine, lysine, phenylalanine, proline, serine, threonine, tyrosine, and valine, respectively; and the designation "=" represents —S—S—bond and the arabic numbers adjacent to the amino acid cords depict the amino acid sequential arrangement as enumerated from the N-terminal.

2. The method according to claim 1, wherein said polypeptide is administered in an amount of from 0.3 to 1.0 mg per kg of body weight per day.

3. The method according to claim 1, wherein said tumor is a sarcoma tumor.

4. The method according to claim 1, wherein said tumor is an EAC (Ehrlich ascites carcinoma).

5. The method according to claim 1, wherein said tumor is a leukemia tumor.

* * * * *